United States Patent [19]

Morris et al.

[11] 4,141,688

[45] Feb. 27, 1979

[54] COMPOSITION, DEVICE AND METHOD FOR DETERMINING REDUCING AGENTS

[75] Inventors: David A. N. Morris; Patricia A. Rupchock; Mark T. Skarstedt, all of Elkhart, Ind.

[73] Assignee: Miles Laboratories, Inc., Elkhart, Ind.

[21] Appl. No.: 823,618

[22] Filed: Aug. 11, 1977

[51] Int. Cl.$^2$ .................. C07D 279/34; G01N 31/22; C07D 265/38
[52] U.S. Cl. .............................. 23/230 B; 23/230 M; 252/408 R; 544/37; 544/102; 544/103; 422/56
[58] Field of Search .......... 23/253 TP, 230 B, 230 M; 544/37, 102, 103; 252/408 R

[56] References Cited

U.S. PATENT DOCUMENTS 3,791,988  2/1974  Josef et al. .................. 23/230 B X

OTHER PUBLICATIONS

Gal, Nature, vol. 138, p. 799 (1936).
Lund et al., Nature, vol. 137, p. 784 (1936).
Rosenberg, Chemistry and Physiology of the Vitamins, pp. 318 to 321, Interscience Publishers, Inc. NY, NY (1942).
Feigl, Spot Tests in Organic Analysis, pp. 390 to 391, Elsevier Pub. Corp. (NY) (1956).
Venkataraman (I), The Chemistry of Synthetic Dyes, vol. II, pp. 761–775, 780–785 and 791–795, Academic Press Inc. NY (1952).
Venkataraman, The Chemistry of Synthetic Dyes, vol. IV, pp. 146–147, Academic Press (1971) NY.
Elliott et al., Journal of Research of the National Bureau of Standards vol. 26, pp. 117 to 128 (Research Paper RP 1364), (1941).
Stuzka et al., Chemical Abstracts vol. 75, Abst. No. 29564 (1971).
Mannelli et al., Chemical Abstracts, vol. 45, cols. 8394 to 8395 (1951).

*Primary Examiner*—John D. Randolph
*Attorney, Agent, or Firm*—Edward H. Gorman

[57] ABSTRACT

A composition, device and method for determining the presence of a reducing agent, such as ascorbic acid, in a test sample are disclosed. The composition comprises certain thiazine and oxazine compounds which, in their oxidized state, are colored, but which become colorless when reduced by a reducing agent. The device comprises a carrier matrix incorporated with the composition, and the method comprises contacting a test sample with the composition device and observing any detectable response such as a color change.

59 Claims, No Drawings

COMPOSITION, DEVICE AND METHOD FOR DETERMINING REDUCING AGENTS

BACKGROUND OF THE INVENTION

1. Field of the Invention

The present invention relates to detecting the presence of a reducing agent, such as ascorbic acid, in a test sample. More specifically, it relates to an analytical device and composition useful for determining the presence of the reducing agent in a liquid sample.

2. Discussion of the Prior Art

The analysis of different physico-chemical systems for the presence of reducing agents has been performed through the years by various methods, and utilizing varied chemistries. Some of these involve wet chemistry techniques, while others, for example C-STIX® reagent strips marketed by the Ames Company Division of Miles Laboratories, Inc., provide dip-and-read convenience.

Of the wet chemistry methods for analyzing the presence of reducing agents, several are of principal importance. These are the reduction of periodic acid, phosphomolybdic acid, Fehling solution, Tollens reagent, Nessler reagent, o-dinitrobenzene, p-nitrosodimethylaniline, selenous acid, and methylene blue. All of these wet chemistry techniques are discussed in Fritz Feigl, Spot Tests in Organic Analysis, Elsevier Publishing Company (1966) and H. R. Rosenberg, Chemistry and Physiology of the Vitamins, Interscience Publishers (1945).

Prior clinical determinations of ascorbic acid include titrations with iodine, 2,6-dichlorophenolindophenol, methylene blue, and by reaction with Folin's reagent, molybdenum-phosphotungstic acid, ferricyanide/ammonium molybdate, phosphomolybdic acid, uranyl acetate, vanadium, sulfanilic acid diazonium salt, sulfanilamide, selenous acid, gold trichloride, mercuric chloride, copper (II) sulfate/ammonium thiocyanate, iron (II) sulfate, iron (III) cyanide, hydrochloric acid (furfural test), cacotheline, permanganate and ferricyanide (Prussian blue method). All of these methods are described in H. R. Rosenberg, Chemistry and Physiology of the Vitamins, Interscience Publishers, New York (1945).

U.S. Pat. No. 3,771,964 describes a test composition and device for determining the presence of ascorbic acid in fluids such as urine. The composition comprises at least one phosphomolybdate salt and a nitrate salt. A dip-and-read device is prepared by incorporating the composition with a dry carrier material such as paper. The presence of ascorbic acid in the test sample will cause the device to turn blue, the color intensity being directly dependent on the concentration of ascorbic acid in the sample.

The present invention was discovered in the course of a research program aimed at finding a new reagent strip chemistry for determining ascorbic acid in urine. Specifically, a continuous response was sought over a range of ascorbic acid concentrations of about 40 to 200 mg%, this range including the ascorbate concentrations usually found in human urine.

SUMMARY OF THE INVENTION

Briefly stated, the present invention comprises a composition, device and method for detecting the presence of a reducing agent, particularly ascorbic acid, in a test sample. The composition comprises an indicator having the structure

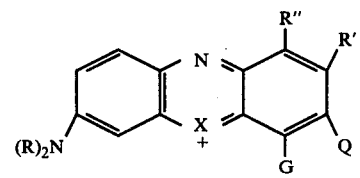

in which
X is O or S, wherein when X is S
R, R' and R", same or different, are H or lower alkyl,
Q is $NH_2$ or N(lower alkyl)$_2$, and
G is H, $NO_2$ or OH;
with the proviso that when X is S, Q is not $N(CH_3)_2$, R is not methyl and G, R' and R" are not H, simultaneously;
and when X is O
R and R', same or different, are H or lower alkyl,
R" is H, COOH, COOR, $CONR_2$ or
R" and R' together form a hydrocarbon ring having 4 to 7 carbon atoms, and
G and Q, same or different are H or OH.

As used herein, the term "lower alkyl" means an alkyl radical having from about 1 to 6 carbon atoms. Thus, lower alkyl includes methyl, ethyl, and all isomers of propyl, butyl, pentyl and hexyl. The device comprises a carrier matrix incorporated with the composition and the method comprises contacting the composition or device with the test sample suspected of containing the reducing agent, and observing a detectable response emanating from the carrier matrix.

DETAILED DESCRIPTION OF THE INVENTION

The indicators which comprise the heart of the present invention are known as thiazine (when X in structure [I] is S) and oxazine (when X in structure [I] is O) dyes. The structures used in this specification show these compounds in their oxidized state, wherein they exhibit deep colors. Upon contact with ascorbic acid or other reducing agents in aqueous solution, these oxidized dyes are converted to a colorless reduced state. Thus, when a compound of this genre is contacted with a test sample containing a reducing agent its color is bleached to an extent dependent upon the amount of reducing agent present. Thus, by observing the degree of bleaching of the indicator, one can accurately estimate the concentration of reducing agent present in the sample.

The Colour Index, third edition, published by the Society of Dyers and Colourists, in conjunction with the American Association of Textile Chemists and Colourists (1971) is a standard, industry-recognized dye index, which cataloques many of the indicators of the present invention. These compounds are listed under "C.I." numbers, and such notations as used herein refer to listings in the Colour Index.

Some examples of thiazine dyes useful in the present invention are Lauth's violet (C.I. 52000), azur A (C.I. 52005) methylene green (C.I. 52020) and toluidine blue (C.I. 52040). Some oxazine dyes particularly suitable for this invention are gallocyanine (C.I. 51030), prune pure (C.I. 51040), gallamine blue (C.I. 51045), celestine blue (C.I. 51050), and Meldola's blue (C.I. 51175).

Although the color fading phenomenon inherent in the presently claimed indicator compounds is, by itself, sufficient to provide a qualitative and semi-quantitative analytical basis, it was found that a still better detectable response can be had if the indicator compound is used in conjunction with an ancillary, or background, dye. Such a dye is neutral red (C.I. 50040). Thus, for example, a carrier matrix incorporated with neutral red and methylene green is initially dark blue, changing to purple, lavender and ultimately red, depending on the presence of a reducing agent and its concentration. Thus, the background dye enables the observer to more easily differentiate the response of the present composition and device by effecting a change from one color to another as opposed to a change in the intensity of a single color. Instead of observing methylene green fade from greenish blue to pale blue, the use of red background dye with methylene green permits the observer to see a change from dark blue to purple to lavender to red.

The carrier matrix employed with the presently-described concepts can take on a variety of forms. Preferably, the carrier matrix is bibulous in nature so that the indicator compound can be incorporated with the matrix as a solution in a suitable solvent such as water, ethanol or chloroform. Thus, the bibulous matrix can be immersed in the indicator solution and dried to form the test device.

Alternatively, a carrier matrix can be printed, either as a continuous coating, in substantially discrete dots, as stripes, etc., with an ink comprising the indicator component and a suitable vehicle. This printing technique is described in U.S. Application Ser. No. 701,403, filed June 30, 1976, and assigned to the assignee of the present application.

Examples of suitable carrier matrix materials are multitudinous. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the paper with part of the reactant system and impregnating the meshwork with other, potentially incompatible reagents. Finally, French Pat. No. 2,170,397 teaches the use of carrier matrices having greater than 50% polyamide fibers therein.

In a preferred embodiment of the test device, the carrier matrix is a porous filter paper such as the commercially available Eaton and Dikeman 222. The device can be prepared by immersing the filter paper in an aqueous solution of an indicator compound, such as methylene green. The indicator solution may additionally contain buffers such as citric acid, phosphoric acid, carbonic acid or their salts, anionic, cationic, and nonionic surfactants, and other ancillary ingredients known to those skilled in the art of preparing dip-and-read type reagent strips.

After immersion in the indicator solution, the thus-impregnated filter paper is dried, as in an air oven. The dried carrier matrix can then be affixed to a support member, such as a strip of polystyrene sheet, which serves as a handle for the reagent-laden carrier matrix. The matrix can be secured to the handle by any suitable means, such as double-faced adhesive tape or a porous overlay.

Any suitable background dye may be used with the present invention, but preferably it is one which is chemically compatible with the indicator compound, and which does not change color in the presence of the reducing agent to be determined. Neutral red satisfies these criteria and has been found to be especially suited to the present invention when the reducing agent analysate is to be ascorbic acid in urine.

The method for using the test device entails immersing it in a test sample suspected of containing a particular reducing agent for about 1 to 30 seconds or more and observing any change in the amount of light absorbed or reflected. A semi-quantitative determination of the reducing agent concentration can be had by comparing the response in the test device to a series of standard color blocks. These color blocks are calibrated for known concentrations of the reducing agent.

The following Examples are provided to describe the presently preferred embodiments of the present invention and to present comparative data showing the relative efficacy of the indicator compounds. The Examples are descriptive only, and are not meant to limit the scope of the invention.

EXAMPLE I — THE TEST DEVICE

A test device in accordance with the present invention was prepared for use in testing urine samples for the presence of ascorbic acid and for determining its concentration.

The carrier matrix was made from filter paper obtained from Eaton and Dikeman, paper no. 204. A piece of this paper measuring approximately 5 × 1¼ inches was immersed in a solution containing the indicator compound, the background dye, and various ancillary components. Specifically, the solution contained the following components dissolved in 10 liters of distilled water.

1.5 g (grams) methylene green (lot no. A6, obtained from Matheson, Coleman, & Bell, Inc.)

0.50 g neutral red (lot no. CX36, obtained from Matheson, Coleman, & Bell, having a dye content of about 68%)

126.95 g $NaH_2PO_4.H_2O$ (obtained from Mallinckrodt)

11.35 g $Na_2HPO_4$ (obtained from Mallinckrodt)

The pH of this solution was measured and found to be 5.8. If necessary, the pH can be adjusted to about 5.8 using 5 M solutions of NaOH or HCl.

The thus-impregnated filter paper carrier matrix was then dried in an air oven at 50° C. for about 20 minutes.

The dried filter paper, which was dark blue in color, was cut into pieces measuring 0.4 × 0.2 inches, rectangular. The matrix pieces were then mounted individually on handles measuring 3½ × 0.2 inches, the handles being made from a clear, colorless, flexible, polystyrene sheet material with a smooth surface. The polystyrene sheet was 7.5 mils in thickness and was obtained from American Can Company. The matrices were mounted on the polystyrene handles through the use of a double-faced adhesive tape obtained from 3M Company, stock no. Y915.

EXAMPLE II — EVALUATION OF THE TEST DEVICE OF EXAMPLE I

In order to determine the efficacy of the test devices prepared in Example I for determining ascorbic acid concentrations in urine on a semi-quantitative basis, the following experiment was performed. Separate urine samples were prepared containing 0, 25, 50, 100, and 200 mg% (milligrams/100 milliliters) of ascorbic acid, respectively. The matrix portions of separate reagent strips prepared in accordance with Example I were dipped into each of the respective urine samples for a period of about 1 to 2 seconds and removed. Each carrier matrix, after it was dipped, was permitted to develop for a period of 60 seconds, whereupon the color was noted.

It was found that, depending on the concentration of ascorbic acid in the urine sample, the initial dark blue color had faded to a noticeable degree, such that the relative concentrations of ascorbic acid in the urine samples could be distinguished one from the other over the range of 0 to 200 mg% by the degree and nature of color change. No color change was noted for 0 mg%. At 25 mg% ascorbic acid the color changed from dark blue to blue with a tinge of purple; at 50 mg% to purple; at 100 mg% to lavender; and at 200 mg% the matrix was red, the color of the background dye. Thus, for an ascorbic acid concentration of 200 mg% the strip had changed from a dark blue to red.

EXAMPLES III — XXV — EVALUATION OF VARIOUS THIAZINE, OXAZINE, AND AZINE DYES AS INDICATORS

A series of experiments was conducted in order to assess the relative utility of a representative number of thiazine, oxazine, and azine dyes as indicator compounds. Surprisingly, the results of the experimental data indicates that only compounds satisfying structural formula [I], supra, were satisfactory for use in a reagent strip for the detection of ascorbic acid in urine.

Sections of filter paper measuring 3 × 4 inches, obtained from Eaton and Dikeman, paper number 222, were impregnated with solutions of the indicators listed in the table. Each indicator compound was made up into a solution of about 50 milligrams of the indicator in about 5 milliliters of a citric acid/sodium citrate buffer solution having a pH of about 4. The filter paper was impregnated in separate areas with 25 microliters ($\mu$l) of each of the buffered indicator solutions. Thus, the filter paper contained a total of 25 spots, each of a different indicator. This resulted in a total of four pieces of filter paper measuring 3 × 4 inches each.

In order to determine the relative performance of each indicator for detecting ascorbic acid, a 25 microliter sample of an ascorbic acid solution in urine was applied to each indicator dot. This solution contained 1 g of ascorbic acid per 100 milliliters of urine (1,000 mg%). The indicators were evaluated by applying the sample of ascorbic acid to a particular indicator dot, waiting for 60 seconds, and observing any color changes. The relative utility of each indicator was assessed by assigning arbitrary values to the rapidity with which the indicator faded. Thus, an indicator which faded very rapidly was assigned an arbitrary value of 5, whereas an indicator which faded little or not at all was assigned an arbitrary value of 1 or 0, respectively. The high ascorbic acid concentration of 1000 mg% was chosen in order to minimize the danger of experimental error. Thus an indicator having a fade rate of 1 at 1000 mg% ascorbic acid would not function (or fade) in a composition or device required to detect ascorbate levels of up to 200 mg%. The results of this experiment are recorded in the table below.

| | | THIAZNINES | | |
|---|---|---|---|---|
| Example | Indicator Compound and Structure | C.I. Number | Obtained from | Fade Rate |
| III | Lauth's violet | 52000 | Pfaltz and Bauer, Inc. Stamford, Connecticut | 5 |
| IV | Azure C | 52002 | Eastman Kodak Co. Rochester, N.Y. | 0 |
| V | Azure A | 52005 | Chroma-Gesellschaft, Schmid and Co. distributed by Roboz Surgical Instrument Co. Washington, D.C. | 5 |
| VI | Azure B | 52010 | Chroma-Gesellschaft, Schmid and Co. distributed by Roboz Surgical Instrument Co. Washington, D.C. | 1 |
| VII | Methylene Blue | 52015 | The G. Frederick Smith Chemical Co. Columbus, Ohio | 1 |
| VIII | Methylene Green | 52020 | | 5 |

-continued

| Example | Indicator Compound and Structure | C.I. Number | Obtained from | Fade Rate |
|---|---|---|---|---|
| IX | New Methylene Blue | 52030 | Matheson, Coleman & Bell Norwood, Ohio | 1 |
| X | Toluidine Blue | 52040 | Pfaltz & Bauer, Inc. Stamford, Connecticut | 5 |

OXAZINES

| Example | Indicator Compound and Structure | C.I. Number | Obtained from | Fade Rate |
|---|---|---|---|---|
| XI | Brilliant Cresyl Blue | 51010 | Allied Chemical & Dye Corporation New York, N.Y. | 1 |
| XII | Capri Blue | 51015 | National Aniline Div. Allied Chemical and Dye Corp. New York, N.Y. | 0 |
| XIII | Gallocyanine | 51030 | Chroma-Gesellschaft, Schmid and Company Distributed by Roboz Surgical Instrument Co. Washington, D.C. | 5 |
| XIV | Prune Pure | 51040 | Matheson, Coleman, & Bell Norwood, Ohio | 5 |
| XV | Gallamine Blue | 51045 | Chroma-Gesellschaft, Schmid and Company Distributed by Roboz Surgical Instrument Co. Washington, D.C. | 5 |
| XVI | Celestine Blue | 51050 | K and K Laboratories, Inc. Plainview, N.Y. | 5 |
| XVII | Meldola's Blue | 51175 | Chroma-Gesellschaft, Schmid and Company Distributed by Roboz Surgical Instrument Co. Washington, D.C. | 5 |
| XVIII | Nile Blue A | 51180 | Pylam Queen's Village, N.Y. | 0 |

-continued

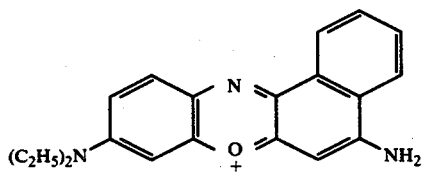

Matheson, Coleman & Bell
Norwood, Ohio

AZINES

| Example | Indicator Compound and Structure | C.I. Number | Obtained from | Fade Rate |
|---|---|---|---|---|
| XIX | Neutral Red | 50040 | National Aniline Div. Allied Chemical & Dye Corporation New York, N.Y. | 0 |
| XX | Azocarmine GFM | 50085 | Chroma-Gesellschaft, Schmid and Company Distributed by Roboz Surgical Instrument Co. Washington, D.C. | 0 |
| XXI | Methylene Violet | 50205 | Chroma-Gesellschaft, Schmid and Company Distributed by Roboz Surgical Instrument Co. Washington, D.C. | 0 |
| XXII | Rhoduline Violet | 50215 | Chroma-Gesellschaft, Schmid and Company Distributed by Roboz Surgical Instrument Co. Washington, D.C. | 0 |
| XXIII | Gossypimine | 50240 | Chroma-Gesellschaft, Schmid and Company Distributed by Roboz Surgical Instrument Co. Washington, D.C. | 0 |
| XXIV | Magdala Red | 50375 | Chroma-Gesellschaft, Schmid and Company Distributed by Roboz Surgical Instrument Co. Washington, D.C. | 0 |

| | | | | |
|---|---|---|---|---|
| XXV | Induline | | 50400 | 0 |
| | 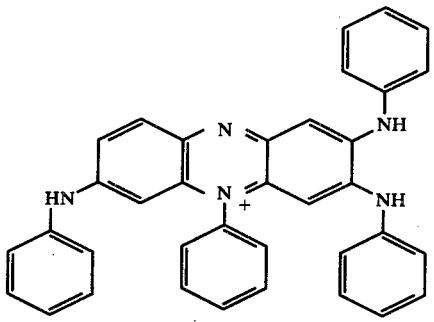 | | Matheson, Coleman, & Bell Norwood, Ohio | |

What is claimed is:

1. A composition for determining the presence of ascorbic acid in a test sample, said composition comprising
   (a) an indicator compound comprising Lauth's Violet, azur A, methylene green, toluidine blue, gallocyanine, or prune pure, and
   (b) a suitable buffer.

2. The composition of claim 1 in which the indicator is methylene green.

3. The composition of claim 1 in which the indicator is gallocyanine.

4. The composition of claim 1 in which the indicator is prune pure.

5. A device for determining the presence of ascorbic acid in a test sample, the device comprising a carrier matrix incorporated with
   (a) an indicator compound responsive to ascorbic acid, and having the structure

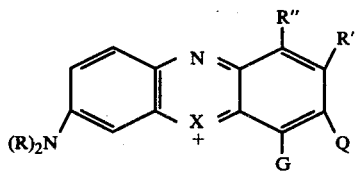

in which X is O or S, wherein when X is S
   R, R' and R", same or different, are H or lower alkyl,
   Q is $NH_2$ or $N(lower\ alkyl)_2$, and
   G is H, $NO_2$ or OH;
with the proviso that when X is S, Q is not $N(CH_3)_2$, R is not methyl and G, R' and R" are not H, simultaneously;
and when X is O
   R and R', same or different, are H or lower alkyl,
   R" is H, COOH, COOR, $CONR_2$ or
   R" and R' together form a hydrocarbon ring having 4 to 7 carbon atoms, and
   G and Q, same or different, are H or OH, and
   (b) a suitable buffer.

6. The device of claim 5 in which X is S.

7. The device of claim 5 in which the indicator compound is Lauth's violet, azur A, methylene green or toluidine blue.

8. The device of claim 5 in which the indicator compound is methylene green.

9. The device of claim 5 in which X is O.

10. The device of claim 5 in which the indicator compound is gallocyanine, prune pure, gallamine blue, celestine blue or Meldola blue.

11. The device of claim 5 in which the indicator compound is gallocyanine.

12. The device of claim 5 in which the indicator compound is prune pure.

13. The device of claim 5 in which the carrier matrix is further incorporated with a background dye.

14. The device of claim 13 in which X is S.

15. The device of claim 13 in which the indicator is Lauth's violet, azur A, methylene green or toluidine blue.

16. The device of claim 13 in which the indicator is methylene green.

17. The device of claim 13 in which the indicator is methylene green and the background dye is neutral red.

18. The device of claim 13 in which X is O.

19. The device of claim 13 in which the indicator compound is gallocyanine, prune pure, gallamine blue, celestine blue or Meldola blue.

20. The device of claim 13 in which the indicator compound is gallocyanine.

21. The device of claim 13 in which the indicator compound is prune pure.

22. The device of claim 13 in which the indicator compound is gallocyanine and the background dye is neutral red.

23. A device for determining the presence of ascorbic acid in a test sample comprising a bibulous paper carrier matrix affixed to a support member serving as a handle, said matrix being incorporated with methylene green as an indicator compound responsive to ascorbic acid, neutral red as a background dye and a buffer capable of producing a pH of about 5.8.

24. A method for determining the presence of ascorbic acid in a test sample comprising
   (a) contacting the sample with a carrier matrix incorporated with:
      (i) an indicator compound responsive to ascorbic acid, and having the structure

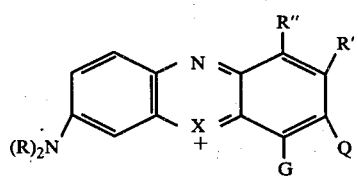

in which X is O or S, wherein when X is S
   R, R' and R", same or different, are H or lower alkyl,
   Q is $NH_2$ or $N(lower\ alkyl)_2$, and
   G is H, $NO_2$ or OH;

with the proviso that when X is S, Q is not N(CH₃)₂, R is not methyl and G, R' and R" are not H, simultaneously; and when X is O;

R and R', same or different, are H or lower alkyl,
R" is H, COOH, COOR, CONR₂ or
R" and R' together form a hydrocarbon ring having 4 to 7 carbon atoms, and
G and Q, same or different, are H or OH; and
(ii) a suitable buffer; and
(b) observing a detectable response.

25. The method of claim 24 in which X is S.

26. The method of claim 24 in which the indicator compound is Lauth's violet, azur A, methylene green or toluidine blue.

27. The method of claim 24 in which the indicator compound is methylene green.

28. The method of claim 24 in which X is O.

29. The method of claim 24 in which the indicator compound is gallocyanine, prune pure, gallamine blue, celestine blue or Meldola blue.

30. The method of claim 24 in which the indicator compound is gallocyanine.

31. The method of claim 24 in which the indicator compound is prune pure.

32. The method of claim 24 in which the carrier matrix is further incorporated with a background dye.

33. The method of claim 32 in which X is S.

34. The method of claim 32 in which the indicator is Lauth's violet, azur A, methylene green or toluidine blue.

35. The method of claim 32 in which the indicator is methylene green.

36. The method of claim 32 in which the indicator is methylene green and the background dye is neutral red.

37. The method of claim 32 in which X is O.

38. The method of claim 32 in which the indicator compound is gallocyanine, prune pure, gallamine blue, celestine blue or Meldola blue.

39. The method of claim 32 in which the indicator compound is gallocyanine.

40. The method of claim 32 in which the indicator compound is prune pure.

41. The method of claim 32 in which the indicator compound is gallocyanine and the background dye is neutral red.

42. A method for determining the presence of ascorbic acid in a test sample comprising
(a) contacting the sample with a test composition comprising
(i) an indicator compound responsive to ascorbic acid, and having the structure

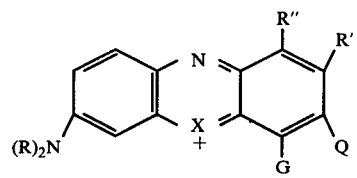

in which X is O or S, wherein when X is S
R, R' and R", same or different, are H or lower alkyl,
Q is NH₂ or N(lower alkyl)₂, and
G is H, NO₂ or OH;
with the proviso that when X is S, Q is not N(CH₃)₂, R is not methyl and G, R' and R" are not H, simultaneously; and when X is O
R and R', or different, are H or lower alkyl,
R" is H, COOH, COOR, CONR₂ or
R" and R' together form a hydrocarbon ring having 4 to 7 carbon atoms, and
G and Q, same or different, are H or OH, and
(ii) a suitable buffer; and
(b) observing a detectable response.

43. The method of claim 42 in which X is S.

44. The method of claim 42 in which the indicator compound is Lauth's violet, azur A, methylene green or toluidine blue.

45. The method of claim 42 in which the indicator compound is methylene green.

46. The method of claim 42 in which X is O.

47. The method of claim 42 in which the indicator compound is gallocyanine, prune pure, gallamine blue, celestine blue or Meldola blue.

48. The method of claim 42 in which the indicator compound is gallocyanine.

49. The method of claim 42 in which the indicator compound is prune pure.

50. The method of claim 42 in which the carrier matrix is further incorporated with a background dye.

51. The method of claim 50 in which X is S.

52. The method of claim 50 in which the indicator is Lauth's violet, azur A, methylene green or toluidine blue.

53. The method of claim 50 in which the indicator is methylene green.

54. The method of claim 50 in which the indicator is methylene green and the background dye is neutral red.

55. The method of claim 50 in which X is O.

56. The method of claim 50 in which the indicator compound is gallocyanine, prune pure, gallamine blue, celestine blue or Meldola blue.

57. The method of claim 50 in which the indicator compound is gallocyanine.

58. The method of claim 50 in which the indicator compound is prune pure.

59. The method of claim 50 in which the indicator compound is gallocyanine and the background dye is neutral red.

* * * * *